US009170219B2

(12) United States Patent
Beck

(10) Patent No.: US 9,170,219 B2
(45) Date of Patent: Oct. 27, 2015

(54) X-RAY DETECTOR SYSTEM FOR ASSESSING THE INTEGRITY AND PERFORMANCE OF RADIATION PROTECTIVE GARMENTS

(75) Inventor: Thomas J. Beck, Catonsville, MD (US)

(73) Assignee: Bar-Ray Products, Inc., Littlestown, PA (US)

( * ) Notice: Subject to any disclaimer, the term of this patent is extended or adjusted under 35 U.S.C. 154(b) by 649 days.

(21) Appl. No.: 13/404,876

(22) Filed: Feb. 24, 2012

(65) Prior Publication Data

US 2012/0219113 A1 Aug. 30, 2012

Related U.S. Application Data

(60) Provisional application No. 61/446,399, filed on Feb. 24, 2011, provisional application No. 61/447,312, filed on Feb. 28, 2011.

(51) Int. Cl.
*G01N 23/223* (2006.01)

(52) U.S. Cl.
CPC ........ *G01N 23/223* (2013.01); *G01N 2223/076* (2013.01)

(58) Field of Classification Search
CPC ......... G01T 1/201; G01T 1/026; G01T 1/023; G01T 1/02; G01T 1/2018; G01N 2223/646; G01N 2223/076; G01N 23/223
USPC .......................................... 378/58; 250/252.1
See application file for complete search history.

(56) References Cited

U.S. PATENT DOCUMENTS

| 6,621,887 | B2 * | 9/2003 | Albagli et al. | 378/42 |
| 2006/0218717 | A1 * | 10/2006 | van den Bosch | 4/558 |
| 2007/0012879 | A1 * | 1/2007 | Testardi | 250/361 R |
| 2007/0170351 | A1 * | 7/2007 | Partain et al. | 250/214 C |
| 2009/0014665 | A1 * | 1/2009 | Fleming et al. | 250/484.5 |

OTHER PUBLICATIONS

Finnerty et al., Protective aprons in imaging departments: manufacture stated lead equivalence values require validation, 2005, European Radiology, vol. 15, pp. 1477-1484.*
Thermo Scientific, FH 40 TG Teleprobe Product Specification, 2007, 2 pages.*
Cartwright et al., The angular dependence of effective point of measurement of a cylindrical scintillation dosimeter with and without a radio-opaque marker for brachytherapy, Mar. 17, 2009, Physics in Medicine and Biology, vol. 54, pp. 2217-2227.*
Gusev, Methods of detecting flaws in x-ray shielding, 1980, Biomedical Engineering, vol. 14, No. 1, pp. 22-24.*

* cited by examiner

*Primary Examiner* — David J Makiya
*Assistant Examiner* — John Corbett
(74) *Attorney, Agent, or Firm* — Barry G. Magidoff; Paul J. Sutton

(57) ABSTRACT

A method for quantitatively testing a radiation shielding garment to determine its radiation shielding integrity, utilizing a fluoroscopic system, the method comprising measuring the amount of radiation passing through the garment at a particular location believed to be possibly damaged; measuring the amount of radiation at one or more locations of the garment believed to be intact; determining the average undamaged transmission if more than one location is tested; and comparing the two values of transmitted radiation to determine whether the first location was damaged beyond an acceptable degree.

11 Claims, 8 Drawing Sheets

X-RAY DETECTOR SYSTEM FOR ASSESSING THE INTEGRITY AND PERFORMANCE OF RADIATION PROTECTIVE GARMENTS

This application claims the benefit of priority pursuant to 35 U.S.C. 119(e) from two U.S. provisional patent applications: Application No. 61/446,399, filed Feb. 24, 2011, and Application No. 61/447,312, filed Feb. 28, 2011.

The present invention relates to a method and a device for quantitatively testing the shielding integrity of flexible radiation protective garments used mainly for protection from x-rays in medical, dental and veterinary environments.

BACKGROUND OF THE INVENTION

Radiation protective shield garments consisting of a flexible polymer matrix loaded with heavy metal in fine particulate form, are widely used in, medicine, dentistry and veterinary medicine, to protect workers from x-ray exposure resulting from working in close proximity to x-ray systems and patients during imaging. The nature of the loaded polymer matrix tends to make the garment susceptible to material fatigue, causing cracks, tears or other internal damage that may compromise the protective function. Regulatory bodies including hospital accrediting bodies in the US have mandated that radiation protective garments be tested for damage, to ensure their integrity, at least once per year. Most commonly, the garments are tested by placing them flat on a smooth surface then imaging them by use of a medical radiography or fluoroscopy system. The operator uses the resulting image to detect damage, but up to now, the test data have been entirely qualitative. Other than obvious tears or cracks, there are no criteria for determining if damage is sufficient to require replacement of the garment.

Usually inspection is done visually with a fluoroscope. Tears or major punctures of the protective material are obvious reasons for discarding a garment. But most defects or damaged areas are more subtle and there are no criteria for determining how much damage should warrant replacement of the protective apron in such cases. Ideally replacement criteria should be based on how much the protection is compromised. Currently, no easy quantitative method for doing this is available; all damage assessment is totally qualitative.

OBJECTS OF THIS INVENTION

It is an object of this invention to provide a quantitative means to determine the radiation shielding integrity of a radiation shielding garment. It is a further object to be able to carry out this test means utilizing a simple and relatively inexpensive additional device together with a fluoroscope generally available where radiological procedures are carried out.

The Solution

The invention provides a quantitative solution that would enable the user to test, any suspicious spot or region with very little change in current procedures, i.e., during fluoroscopic inspection The device would consist of a x-ray sensor on an extended arm with a fluoroscopically visible reticule surrounding the sensor at the end. Under fluoroscopic guidance, the operator places the reticule over the suspicious area and acquires a measurement. A nearby reference region with no obvious damage is tested in the same fashion. The percentage difference in transmission between damaged and undamaged areas is reported to the operator. Rejection criteria would be based upon the extent of the increased transmission at the area being checked, relative to the reference area. The user or a standards body might select what threshold criterion indicates a rejection of the apron.

General Statement of the Invention

The present invention provides a method for quickly and quantitatively determining the amount of loss in protection of a given damaged region of a shielding garment. The invention consists of an x-ray transparent, x-ray sensor, preferably with a reticule visible on a fluoroscopic image. The sensor and reticule are connected by a wand to a handle, the wand extends so that the operator holding the handle can be located in a protected position outside the direct x-ray field. Under fluoroscopic guidance the user places the reticule over an apparently damaged region of the garment and a transmission measurement is taken. The x-ray transmission is then compared to that of a reference undamaged region, or preferably several undamaged regions, on the same garment as the damaged area. Results can be expressed as the percentage difference between the damaged and undamaged regions of the garment. A preset threshold increase in transmission is used as a trigger level to determine if damage is sufficient for concern. The device includes the capability for marking locations on the garment, e.g., with a washable ink to indicate where damage is located, using an externally controlled marker centered at the location of the center of the sensor.

A sensor element must have sufficient sensitivity to detect fluoroscopic fluence through at least a 0.5 mm lead apron with high precision, with exposure times of preferably less than one (1) second. The light guide and sensor must be relatively invisible; (low contrast) on fluoroscope image so as to have minimal effect on intensity changes induced by any automatic brightness system.

The reticule will have high contrast but should be present only at the margins of the sensor element. The light guide is internally lined with an optically reflective material, and the outer surface of the light guide is coated with a light-tight coating to ensure that no stray light reaches the diode.

Measurement Concept

The measurement is normally not absolute but is designed to compare quantitatively transmitted intensities that are deemed to be significant from a radiation protection perspective. It can thus be used to compare various shielding products with differing levels of protection, for their protection effectiveness based upon the intended level of protection for that particular shielding product.

BRIEF DESCRIPTION OF THE DRAWINGS

The following drawings.

Referring to FIG. 1, this is an overall picture of a system for carrying out the tests of the present invention, including a figure of an operator;

FIG. 2 is a top view of the radiation detector implement used in the overall system of FIG. 1;

FIG. 3 is a side view of the radiation detector implement of FIG. 2;

FIG. 4 is a diagrammatic view showing the operating elements of the detector implement of FIG. 2;

FIG. 5 is a diagrammatic view of a subsystem within the detector implement of FIG. 2 for marking a tested area;

FIG. 6 is a diagram showing the alternative detection means within the detector implement of FIG. 2; and FIG. 7 in an enlarged top view of the handle end, showing the control and local viewing screen for the detector implement of FIG. 2.

DETAILED DESCRIPTION OF THE INVENTION

Figure 1:
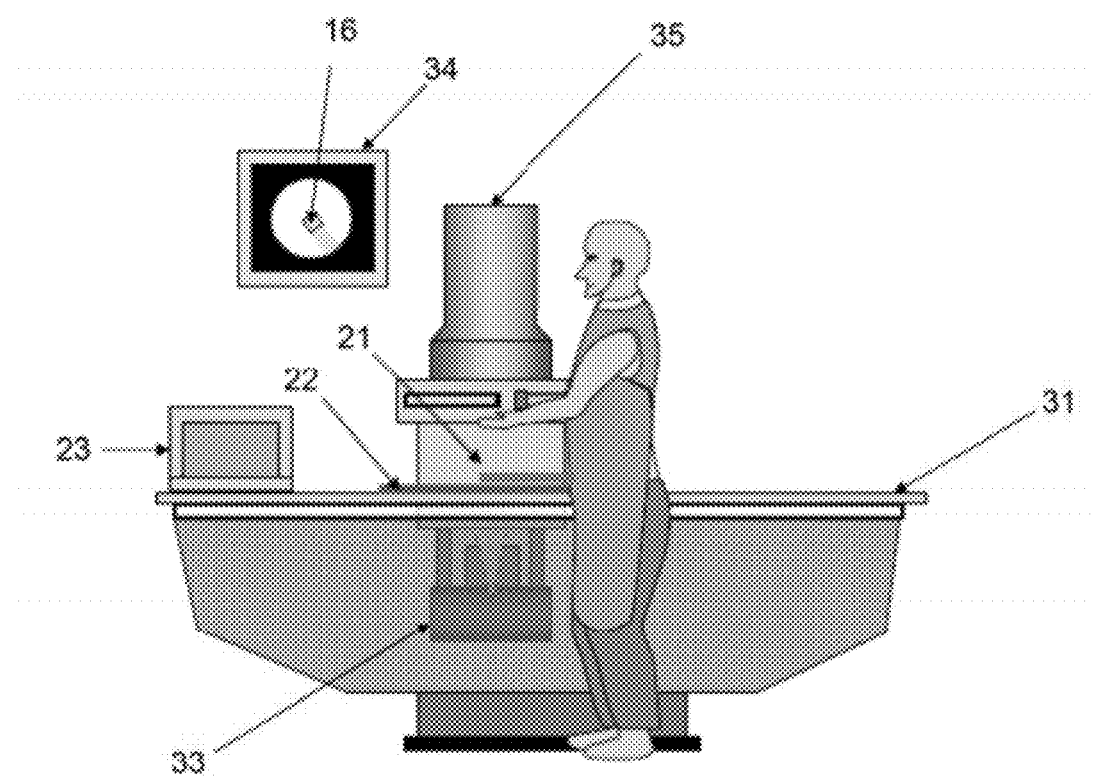
FIGS. 1-7, show examples of designs for this invention and a method of use of the invention.
Figure 2:
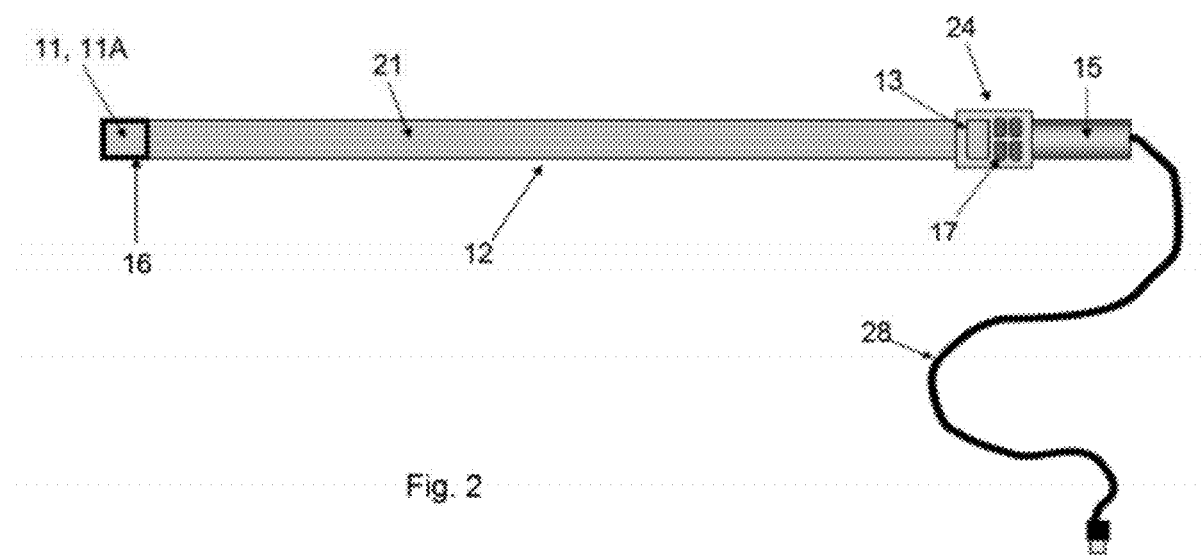
Figure 3:
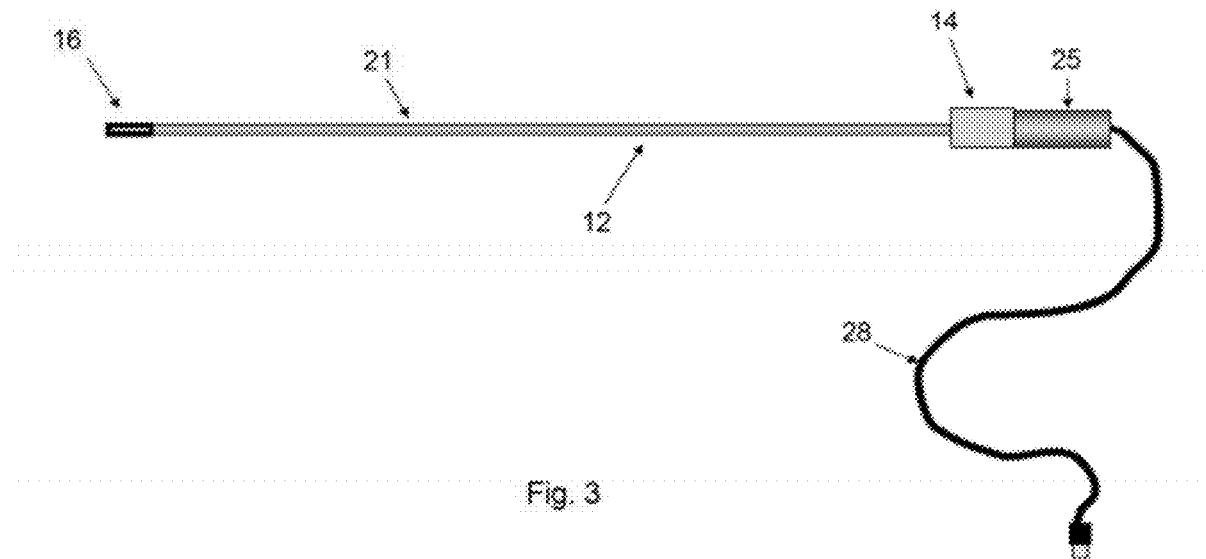
Figure 4:
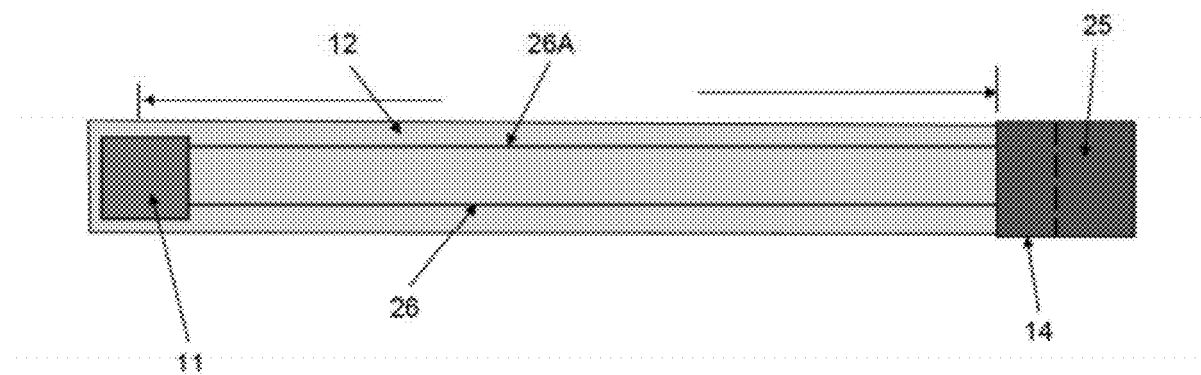
Figure 4A:
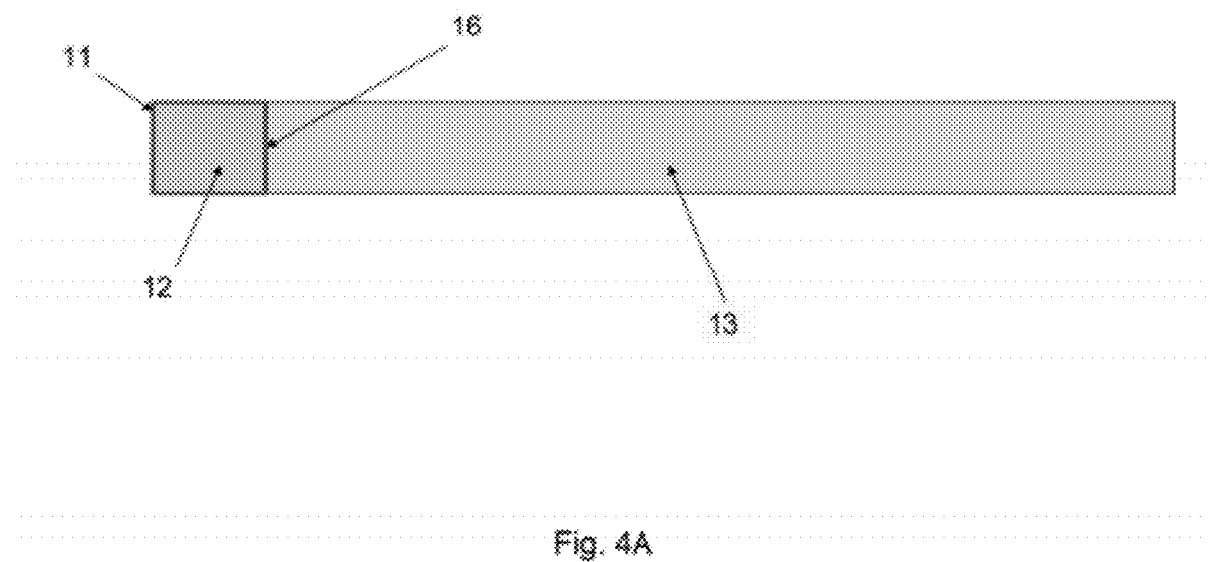
FIG. 4A is a diagrammatic view showing alternative operating elements of the detector implement of FIG. 2.

Referring to FIG. 1, this console unit includes a Table 31, upon which may be placed, in spread-out form, a radiation shield, such as an operator's apron, indicated by the numeral 22, to be tested. X-radiation is generated from the x-ray tube 33, below the table 31, and passes through the shield 22 being tested. The field for the x-rays on the table top 31 is larger than the area to be tested on the apron shield 22. The area of the sensor is outlined by a copper wire reticule 16 visible on the fluoroscopic image monitor 34 on the detector implement 21 of the upper surface of the shield being tested, as the outline of an, e.g., copper wire reticule. The outer end of the detector implement, generally indicated in FIG. 1 by the numeral 21, is placed over the area to be tested; in a preferred embodiment, the detector implement is connected to a portable computer 23 where the comparison between measurements is implemented in software for display on the computer screen.

In one preferred embodiment, the x-ray sensor consists of an organic p-n junction semiconductor plated on a preferably x-ray transparent polymer substrate, and is coated with a conductive material such as aluminum or ITO (indium tin oxide). The sensor can be of the type that is directly an x-ray sensitive diode, or it can be coupled to an adjacent scintillator material such as a green emitting plastic scintillator such as San Gobain BC428 or Eljen 260 with a light measuring photodiode. Alternatively the scintillator might be Polyethylene naphthalate (PEN), which may also function as the supporting substrate for the organic diode material, with a transparent coating of ITO to form one electrode. The resulting x-ray sensor can be mounted on the end of a flat plastic wand 20-30 cm in length and preferably incorporates x-ray transparent aluminum foil, or conductive polymer, electrodes, connecting to a sensitive electrometer at the opposite end of the wand. If a scintillator is used, the entire length of the wand is preferably wrapped in a radiation-transparent optically opaque material to prevent spurious visible light from reaching the photodiode.

The detector implement, generally indicated as 12, includes a handle 15, a control and display section 24, a long rectangular wand 12, at the end of which is supported a radiation sensor element 11, surrounded by a, e.g., copper wire reticule 16. The sensor element is generally a square surface and in the light-emitting embodiment, includes a plastic scintillator 11a and a light sensitive silicon photodiode 14, located at the end of a transparent light guide 15, or an organic semi-conductor sensitive to light, adjacent to the scintilators 11a, so as to generate an electronic signal substantially proportional to the strength of the impinging radiation passing through the shielding garment at the location being tested.

The sensor is controlled by use of the function buttons 7 on the console area 4 and includes a display screen that displays a value indicating the amount of radiation passing through the tested area as well as user function operational modes. An electronic controller system of a conventional sort is maintained in the area 17. Data from the implement 12 are passed through the data transmission line 28 to the computer 23, where data is accumulated and maintained, including a record of the location of each area tested. The detector wand 21 includes at its distal end either a square organic semi-conductor that is x-ray sensitive, or a combination of a plastic scintillator that emits light directly proportional to the amount of radiation detected, and a light-sensitive sensor that measures the scintillator light emissions. Both of these are well known in the art and need no further description. In the event that a silicon sensor is used, the optical light guide will carry the scintillator light back to the sensor in the handle 14. If a direct x-ray radiation detecting organic semi-conductor is included as the sensor 24, or if the sensor records the scintillator light with a light sensitive organic semi-conductor 24, the electronic signal is passed back along conductors present in the wand from the sensor to the electronics section 17.

Figure 5:
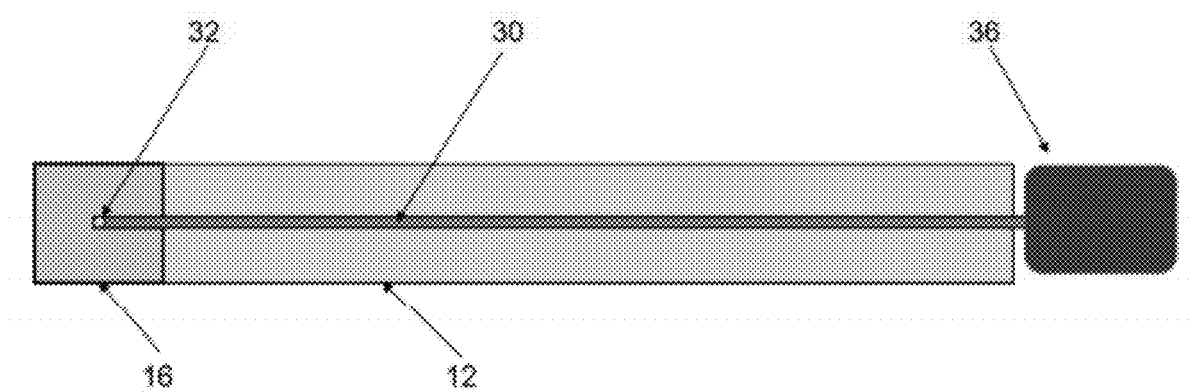
Figure 6:
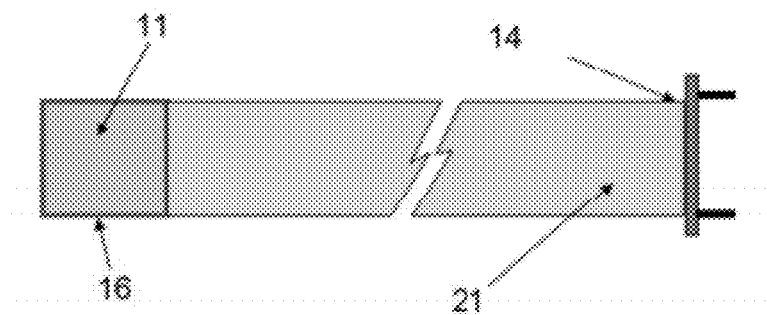
Figure 7:
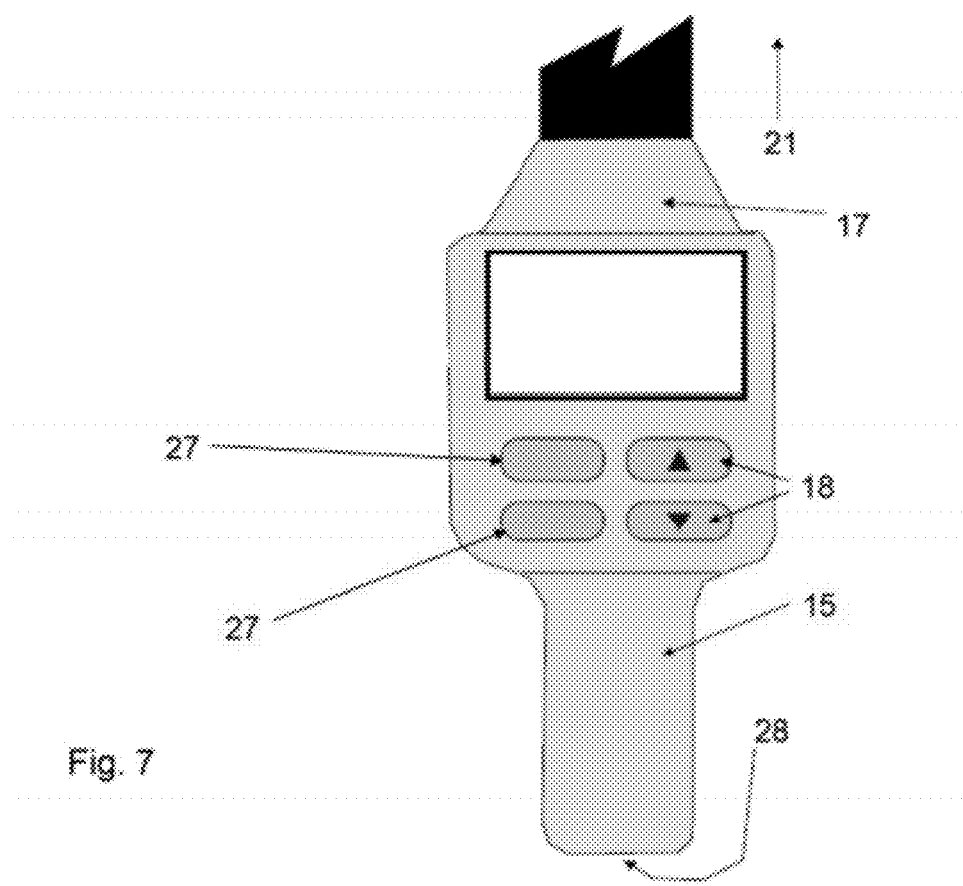

The detector implement also preferably includes a subsystem for physically marking, for example, with a washable ink, an area of a shield that was tested. One such sub-system is shown in FIG. 5 herewith, and includes a pressurized ink reservoir 36 and a duct 30 for carrying ink to a spray nozzle 32 which will act on command by the operator. Such command can either be provided electronically using one of the control buttons 27, to operate a piezoelectric pump, or manually by physically depressing a pressure pump. The nozzle 32 is preferably centered within the reticule 16 area and is x-ray transparent.

When carrying out the test of the present invention, the outer end of the detector implement 12 includes a reticule formed of thin, e.g. 1/16 inch, copper wire surrounding, e.g., a plastic Bicron BCF-20 scintillator, generally available in a size of 25 mm square. Similarly, a Bicron BCF-98 optical light pipe, 3 mm thick, can be used to carry light emitted by the scintillator back to a sensor, generally a photodiode, in the handle/control portion 14/15 of the detector. The light pipe mates with the scintillator 11a in the usual fishtail connection, using optical cement. Generally, the surface of the scintillator light pipe assembly is coated with titanium dioxide reflective material and the outer surface is coated with a black polymeric light sealer to prevent extraneous light from entering the system.

Preferably, a mechanically rigid outer frame, such as would be formed from a polycarbonate resin, can be provided on the outside of the entire wand. The light carried by the light tube can be measured, for example, by a readily available photodiode, such as a Hamatsu S2387-130R diode. The optical light pipe can be, for example, 3 mm thick with a 25×350 mm width and length. The photodiode 14 is connected to the electronics 14, including an amplifier integrating capacitor and an analog to digital converter (ADC) as well as a sampling control module (not shown). The raw data can be displayed on the screen 13, providing the measurement of the radiation detected. The buttons 17 provide a means to scroll through the function menu on the display screen 13, as well as to select a particular measurement for transmission to the main computer 23, and a button to capture the measurements. The sensor can be connected to a source of electricity in the facility via the data cable 25, or can be powered by batteries, encased in the handle 15. Power inputs can be provided, for example, through the conventional USB connection 28. The operator, in addition, has a video monitor and a small video camera that displays the entire system and the measurements and the location of the measurements are recorded therein.

In an alternative embodiment, a square x-ray sensitive semi-conductor diode can generate directly signals to the electronics system 25 via the signal wires 26, 26A. The raw data from either sensor unit can be fed to the computer 23, which can generate the results, calculated from the raw data.

The system is extremely accurate in that it provides a means for quantitative testing of the entire surface of a shield by taking tests at random locations to determine the overall radiation transmission and then comparing that overall transmission with the transmission through a particular area that may appear to be damaged, as a result of a fluoroscopically visual or tactile review. This is often the case with this type of radiation shield material where some type of abrasion or undesired folding has caused a rupture in the continuous shield effectiveness.

The determination can be made by comparing the overall radiation transmission of areas that appear to be undamaged, with areas that appear to be worn or broken in some fashion.

To summarize, one example of the procedure utilizing the system of this invention, as shown in FIG. 1, is as follows:

1. A test apron 22 is placed on the fluoroscope console's tabletop 31 in a single layer and is smoothed to eliminate any wrinkles and folds 2. Suspect regions are identified on the fluoroscopic image as shown on the display monitor 34, which will show as a brighter spot, or as a darker spot.

3. For example, the apron is positioned on the fluoroscope table 31 and the fluoroscope including the x-ray source and image receptor is centered over the suspect region. Generally available clinical fluoroscopes allow for calibrated complementary movement of the x-ray source and fluoroscope sensor over the length and width of the fluoroscope table, thus allowing for obtaining a fluoroscopic image over every portion of any material or person on the table.

4. The detector implement 21 is manipulated so that the reticule 16 is centered over the suspect region and the region and reticule are visible on the display monitor 34 and through the sensor.

5. The button 17 on the handle 15 is pressed to record the radiation exposure through the apron 22 at that point 6. Measurement is repeated at nearby, undamaged regions, and all of these readings are directed from the detector implement 21 to the computer 23, to provide a comparison utilizing a suitable program, to compare the potentially damage area with the apparently undamaged areas, and the intended shielding level of the garment. The results are provided on the screen of the computer 23.

7. If the operator desires, a button on the control is pressed, releasing a, for example, water soluble dye to indicate the suspect area on the apron at the position of the reticule, if the computer indicates that the measured area transmits more radiation than is allowed by the pre-determined defect criteria.

It will be readily understood that the specific details of the components of the detector implement described above and in the drawings are not required in order to form the present invention. It should be noted that a different shapes and different materials for the various components may all be within the scope of this invention. It will therefore be readily understood that the present invention is not limited to the particular elements and materials shown and described hereinabove.

The various aspects, characteristics and architecture of the device of the present invention have been described in terms of the embodiments described herein. It will be readily understood that the embodiments disclosed herein do not at all limit the scope of the present invention. One of ordinary skill in the art to which this invention belongs can, after having read the disclosure, and reviewed the drawings, may readily implement the device and method of the present invention using other implementations that are different from those disclosed herein but which are well within the scope of the claimed invention, as defined by the following claims.

The inventions being claimed are as follows:

1. A method for quantitatively testing a suspicious area or region on a radiation shielding garment, by utilizing a fluoroscopic inspection, the method comprising
   measuring the amount of radiation transmitted through the garment at a particular location believed to include possible damage based upon a fluoroscopically visual or tactile examination;
   measuring the amount of radiation transmitted through at least one area location on the garment believed to be undamaged following a visual or tactile examination;
   comparing the two measured values of transmitted radiation to determine whether the first area location was damaged; and
   determining the amount of radiation passing through the garment at each particular area location, using an x-ray absorbing reticulated scintillator coupled to a light-sensitive sensor located at a distal end of an optical light guide, so that the sensor receives the light generated by the scintillator, whereby the amount of radiation transmitted at that location is measured as light expressed by the scintillator, the reticulated scintillator having a surface area substantially equal to the area location.

2. The method of claim 1, further comprising measuring the amount of radiation passing through the garment at a plurality of such undamaged areas of the garment; taking an average of the measurements of such undamaged areas, and comparing the average with the measured value of transmitted radiation at the visually damaged area, to determine whether the first location was damaged to a predetermined extent.

3. The method of claim 1, wherein the measuring of the amount of radiation passing through the garment at a particular location believed to be possibly damaged, is determined as the x-ray photoconductance in an x-ray sensitive organic semiconductor, caused by the radiation passing through the garment at that measurement location.

4. The method of claim 1, wherein the measuring of the amount of radiation passing through the garment at a particular location believed to be possibly damaged, is determined by a light-sensitive sensor coupled to an adjacent x-ray absorbing scintillator and a light measuring photodiode; whereby the amount of radiation transmitted at that location is measured as light expressed by the scintillator.

5. The method of claim 1, wherein the light meter is a light measuring photodiode open to a second end of the optical light guide.

6. The method of claim 1, further comprising temporarily marking a suspicious region on the outside of the garment so that it can be inspected visually after the measurement is taken.

7. A detector implement for use with a fluoroscope to measure radiation transmission through a radiation shield, the implement comprising a handle, a control and display section extending from the handle, a long rectangular wand, connected at one end to the control and display section and at the second end supporting a radiation sensor element; an x-ray absorbing reticule surrounding the sensor element; and data connectors operationally connecting the sensor element to the control and display section, whereby when the sensor is exposed to radiation, it generates an electronic signal substantially proportional to the strength of the impinging radiation, which is carried by the connectors to the control and display section.

8. The detector implement of claim 7, further comprising a marking subsystem, the subsystem comprising a reservoir of marking material; a nozzle for the marking material located so as to mark an area centered within the reticule; and a pump to move the marker material from the reservoir and out the nozzle, to mark an area tested for radiation transmission.

9. A method for quantitatively testing, by utilizing a fluoroscopic inspection system, the radiation shielding effectiveness of an area of a radiation shielding garment believed to have a defect caused by damage to the garment, as determined from a visual or tactile examination of a suspicious area or region on a radiation shielding garment; the method comprising placing the garment in the path of a beam of ionizing radiation, between the source of the beam and a radiation receptor, measuring the amount of radiation transmitted through the garment at the particular suspicious area or region believed to be possibly damaged; measuring the amount of radiation transmitted through a location on the garment believed to be undamaged following a visual or tactile examination; and comparing the two measured values of transmitted radiation to determine whether the first location was damaged; wherein the quantity of radiation passing through the garment at a particular location, is determined by having a light-sensitive sensor coupled to an adjacent x-ray absorbing reticulated scintillator attached to the distal end of an optical light guide and a light meter open to a second end of the optical light guide; whereby the amount of radiation transmitted at that location is measured as light expressed by the scintillator.

10. A detector implemented for use with a fluoroscope to measure radiation transmission through a radiation shield resting upon a fluoroscope table, the implement comprising:
 a handle,
 a control, and
 display section extending from the handle,
 a long wand extending from, and connected at one end to, the control and display section, the wand supporting at the distal end from the control and display section, a radiation sensor element surrounded by an x-ray absorbing reticule; and
 data connectors operationally connecting the sensor element to the control and display section;
 the radiation sensor element is selected from the group consisting of
  electronic sensors that, when exposed to radiation, generate an electronic signal substantially proportional to the strength of the impinging radiation,
  which also include electronic connectors to the control and display section, and
  light emitting scintillators that emit light of a brightness proportional to the strength of the impinging radiation, which further includes
  an x-ray sensitive diode coupled to the adjacent scintillator material,
  an optical light guide forming the wand and a light sensitive sensor element at the distal end of the optical light guide from the scintillator, adjacent the control and display section,
  wherein the scintillator, the electronic sensor and the light guide are each substantially radiation transparent, and
  a radiation transparent but optically opaque material surrounding the optical light guide.

11. The detector implement of claim 10, wherein x-ray sensor comprises an organic p-n junction semiconductor plated on a preferably x-ray transparent, polymer substrate, coated with a conductive material such as aluminum or indium tin oxide.

* * * * *